US009562840B2

(12) United States Patent
Tabis et al.

(10) Patent No.: US 9,562,840 B2
(45) Date of Patent: Feb. 7, 2017

(54) HIGH PRECISION RECIPROCATING BOB VISCOMETER

(71) Applicant: CAMBRIDGE VISCOSITY, INC., Medford, MA (US)

(72) Inventors: Janusz Tabis, Winchester, MA (US); Peter O'Shea, Medford, MA (US); Daniel A. Airey, Woburn, MA (US); Viachaslau Urvantsau, Fontenay le Marmion (FR)

(73) Assignee: Cambridge Viscosity, Inc., Medford, MA (US)

( * ) Notice: Subject to any disclaimer, the term of this patent is extended or adjusted under 35 U.S.C. 154(b) by 104 days.

(21) Appl. No.: 14/593,454

(22) Filed: Jan. 9, 2015

(65) Prior Publication Data

US 2016/0161389 A1    Jun. 9, 2016

Related U.S. Application Data

(60) Provisional application No. 62/087,044, filed on Dec. 3, 2014.

(51) Int. Cl.
| | | |
|---|---|---|
| *G01N 11/16* | (2006.01) | |
| *G01N 11/10* | (2006.01) | |
| *G01D 5/20* | (2006.01) | |

(52) U.S. Cl.
CPC ............. *G01N 11/162* (2013.01); *G01N 11/10* (2013.01); *G01D 5/204* (2013.01)

(58) Field of Classification Search
CPC ........ G01N 11/162; G01N 11/16; G01N 11/10
(Continued)

(56) References Cited

U.S. PATENT DOCUMENTS

| 3,073,150 A | 1/1963 | Fenn |
|---|---|---|
| 3,677,070 A | 7/1972 | Norcross |

(Continued)

FOREIGN PATENT DOCUMENTS

| GB | 2058341 | 4/1981 |
|---|---|---|
| GB | 2204701 | 11/1988 |
| WO | 93/02347 | 2/1993 |

OTHER PUBLICATIONS

"Viscometer," Wikipedia, http://en.wikipedia.org/wiki/Viscometer.
(Continued)

*Primary Examiner* — John Fitzgerald
*Assistant Examiner* — Gedeon M Kidanu
(74) *Attorney, Agent, or Firm* — Gunn, Lee & Cave, P.C.

(57) ABSTRACT

A high precision, reciprocating bob viscometer is shown that has two coils (A and B) encircling a reciprocating bob. Coil A is energized with a combined sinusoidal and DC signal, while coil B senses the position of the reciprocating bob, then the functions of coils A and B are reversed. By use of a large digitally-generated near resonance frequency sinusoidal signal, noise is reduced because there is no need for amplification. The sensed signal amplitude measurement is in the digital time domain instead of through analog amplitude measurements, which further eliminates signal noise. These advancements provide faster, highly accurate, low noise measurements of bob position and velocity to determine fluid/gas viscosity and related properties using a reciprocating bob viscometer. These related properties include measurements of density, shear sensitivity, yield stress, and other measurements described in prior art patents.

1 Claim, 5 Drawing Sheets

(58) Field of Classification Search
USPC .......................................................... 73/54
See application file for complete search history.

(56) References Cited

U.S. PATENT DOCUMENTS

| | | | |
|---|---|---|---|
| 4,484,468 A | 11/1984 | Gau et al. | |
| 4,557,142 A | 12/1985 | Hensley et al. | |
| 4,627,272 A | 12/1986 | Wright | |
| 4,860,238 A * | 8/1989 | Kraker | G06F 7/548 |
| | | | 708/276 |
| 4,864,849 A | 9/1989 | Wright | |
| 4,992,716 A * | 2/1991 | Ellis | G05B 19/39 |
| | | | 318/592 |
| 5,698,773 A | 12/1997 | Blom et al. | |
| 6,584,831 B1 | 7/2003 | Kasameyer et al. | |
| 6,767,511 B1 | 7/2004 | Rousseau | |
| 6,776,028 B1 | 8/2004 | Lukay | |
| 6,892,213 B2 * | 5/2005 | Huang | G06F 1/022 |
| | | | 708/276 |
| 7,286,871 B2 * | 10/2007 | Cohen | A61B 5/04004 |
| | | | 600/300 |
| 7,614,285 B2 * | 11/2009 | Airey | G01N 11/10 |
| | | | 73/54.23 |
| 7,775,976 B2 | 8/2010 | Fuller et al. | |
| 8,193,810 B2 * | 6/2012 | Otake | G01R 33/34046 |
| | | | 324/307 |
| 2005/0092081 A1 * | 5/2005 | Spanke | G01F 25/0061 |
| | | | 73/290 V |
| 2007/0194781 A1 * | 8/2007 | Zhitomirskiy | G01D 5/204 |
| | | | 324/207.17 |
| 2008/0236254 A1 * | 10/2008 | Airey | G01N 11/10 |
| | | | 73/54.23 |

OTHER PUBLICATIONS

"Programmable, Isolated Voltage-to-Current Converter," Analog Devices, 1B22, Rev. B, pp. 1-4.

Laesecke, Arno and Cousins, Dylan S., "Wide Ranging Viscosity Measurements of Rocket Propellant RP-2," Journal of Propulsion and Power, vol. 29, No. 6, Nov.-Dec. 2013, pp. 1323-1327.

* cited by examiner

HIGH PRECISION RECIPROCATING BOB VISCOMETER

CROSS-REFERENCE TO RELATED APPLICATIONS

This application claims priority to U.S. Provisional Application for Patent No. 62/087,044, filed on Dec. 3, 2014, entitled "High Precision Reciprocating BOB Viscometer."

BACKGROUND OF THE INVENTION

1. Field of the Invention

The present invention relates to viscometers and, more particularly, to high precision reciprocating bob viscometers.

2. Description of the Prior Art

A viscometer is an instrument used to measure the viscosity of a fluid or gas. For liquids with viscosities that vary with a rate of shear, an instrument called a rheometer is used. A viscometer typically measures the fluid/gas' resistance to deformation by shear or tensile stress, while a rheometer measures relationships between deformations and stresses. The drag caused by the relative motion of a fluid/gas over a surface is a measure of viscosity of the fluid/gas.

Rheological characteristics of fluids have been the subject of various studies for many years. Measurements have long been made in laboratories to characterize fluids, whether old or newly developed. Fluid/gas' resistance to deformation by shearing is one of the measurements made in a viscometer.

Many different types of viscometers have been developed in the past. In general, either the fluid remains stationery and an object moves through the fluid, or the object is stationery and the fluid moves past the object. The drag caused by relative motion between the fluid and a surface is a measure of the viscosity of the fluid. Viscometers developed in the past, including the following:
1. U-tube
2. Falling Sphere
3. Falling Ball
4. Falling Piston
5. Oscillating Piston
6. Vibrational
7. Rotational
8. Electromagnetically Spinning Sphere
9. Bubble
10. Rectangular-slit Each of these above-listed viscometers has certain advantages and disadvantages. This particular invention is directed towards the oscillating piston viscometer developed by Cambridge Viscosity, Inc. as described by the company's prior patents. The sensor is a measurement chamber with a magnetically moveable piston or bob. Measurements are taken after a sample is introduced into the measurement chamber where the piston/bob resides. The piston/bob is magnetically driven in an oscillatory motion within the measurement chamber with a controlled magnetic field. The fluid being tested causes a shear stress due to the piston/bob moving through the fluid. Travel time for the piston/bob is measured. The construction parameters of the piston/bob and the measurement chamber, the strength of the magnetic field and the travel distance of the piston/bob are all used to compute the viscosity according to Newton's Law of Viscosity.

The oscillating piston/bob viscometer is particularly well suited for measuring small samples of fluids to be tested in laboratory conditions. Also, the oscillating piston/bob viscometer is particularly adapted to measure high-pressure viscosity and/or high-temperature viscosity in either laboratory or process environments.

In the oscillating piston/bob viscometer, mutual inductance between a drive coil and a monitoring coil is used to determine the position of the piston/bob, which piston/bob contains ferromagnetic material. In prior oscillating pistons/bob viscometers, a comparison is made between (1) the instantaneous voltage induced into the sensing coil and (2) the predetermined fraction of the peak value that the induced voltage achieved during the current piston/bob stroke.

Also, in prior oscillating piston/bob viscometers, the driving coil would have a small AC voltage superimposed on a large DC voltage. A very small AC voltage that is induced in the sensing coil is amplified together with noise. The amplitude of this relatively noisy signal would then be used to sense the piston/bob's position and velocity as it moves through the fluid or gas. The amplified noise made the obtaining of an accurate viscosity measurement difficult.

BRIEF SUMMARY OF THE INVENTION

It is an object of the present invention to provide an oscillating piston/bob viscometer to measure the viscosity of fluids and gases.

It is a further object of the present invention to provide an oscillating piston/bob viscometer that is very accurate when measuring viscosity and other properties of fluids and gases.

It is a further object of the present invention to provide an oscillating piston/bob viscometer that due to its accuracy requires fewer piston/bob reciprocations to achieve faster measurement response.

It is yet another object of the present invention to reduce noise from an oscillating piston/bob viscometer by directly changing the signal being measured to a digital form without using an A/D converter.

It is still another object of the present invention in an oscillating piston/bob viscometer to maximize the AC component in the sense signal that it does not need to be amplified together with noise.

In the present invention, two coils that have a mutual inductance encircle the oscillating piston/bob. A drive or energizing voltage is changed to current in a voltage to current converter. The output signal from the voltage to current converter is fed through a coil selector to either Coil A or Coil B. Coil A will be energized with a combination DC and AC current causing the bob to move in a cylinder. The sensed signal in Coil B via changes in mutual inductance as the bob is moving, will determine the location of the bob inside of the cylinder. Once the bob has traveled a certain distance as detected in the sensing coil A or B, the functions of the two coils will be reversed, thereby driving the piston/bob in the opposite direction. The time that it takes for the piston/bob to travel in a cylinder filled with the fluid/gas being tested determines the viscosity of the fluid/gas.

DESCRIPTION OF THE PREFERRED EMBODIMENT OF THE INVENTION

Figure 1:
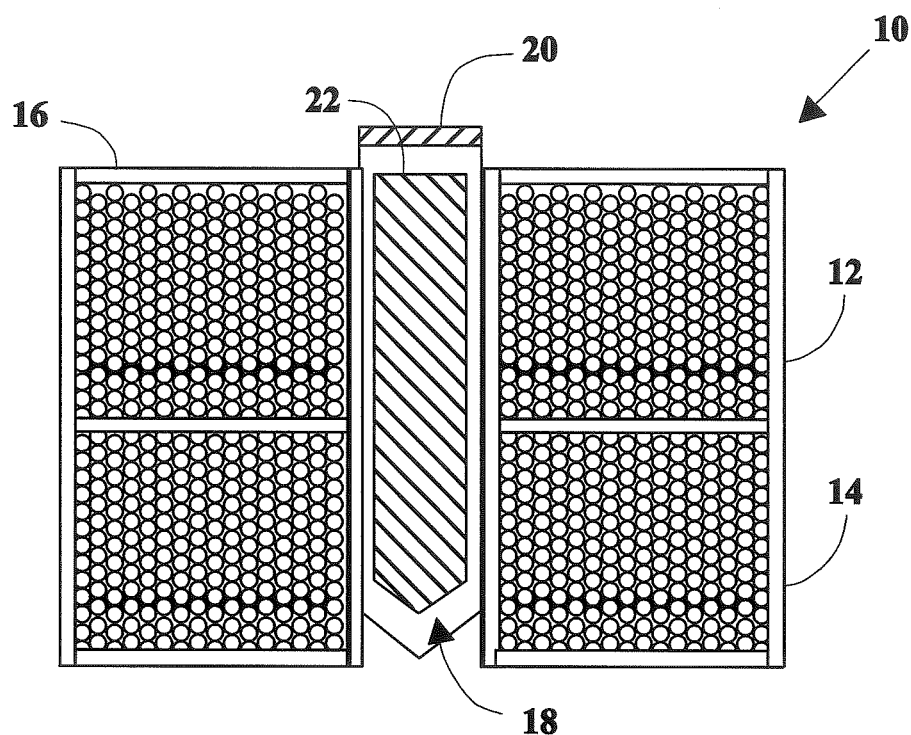
FIG. 1 is a simplified cross-sectional view of one type of reciprocating-bob sensor's coil-and-bob assembly shown in the prior art.

FIG. 1 is a cross-sectional view of one type of reciprocating bob sensor 10 in a coil-and-bob type viscometer. The external shape of the reciprocating bob sensor 10 is generally cylindrical with two separate coils 12 and 14 displaced axially from each other. The coils 12 and 14 are insulated within housing 16 of the reciprocating bob sensor 10. In the center of the cylindrical coils 12 and 14 is a sample well 18. At the mouth of the sample well 18 is a bob-retention spider 20 that keeps the ferromagnetic bob 22 inside the sample well 18. By proper operation of the coils 12 and 14, the ferromagnetic bob 22 will reciprocate inside of sample well 18 moving against the liquid being tested to create a viscous drag. The reciprocating bob sensor 10 just described is shown in the prior art.

In the prior art, a large DC signal and a small AC signal were applied to one of the coils 12 or 14 and the other coil sensed a very small AC signal. Because the small AC signal in the sensing coil 14 or 12 was then amplified, noise picked up by the sensing coil was also be amplified. In an analog type amplifier, the noise as well as the AC signal may be amplified many times.

Figure 2:
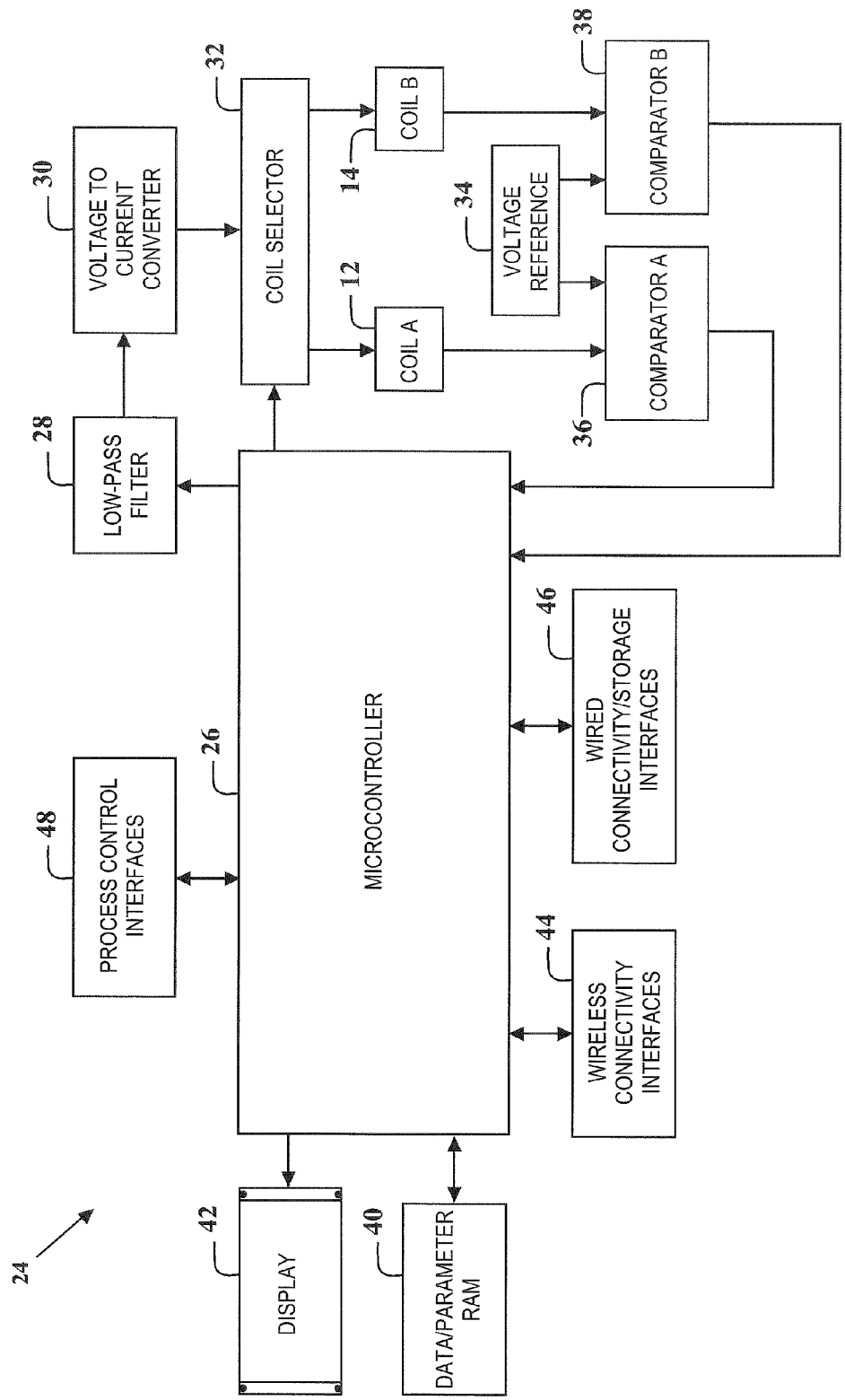
FIG. 2 is a block diagram of the circuitry of the viscometer.
Figure 5:
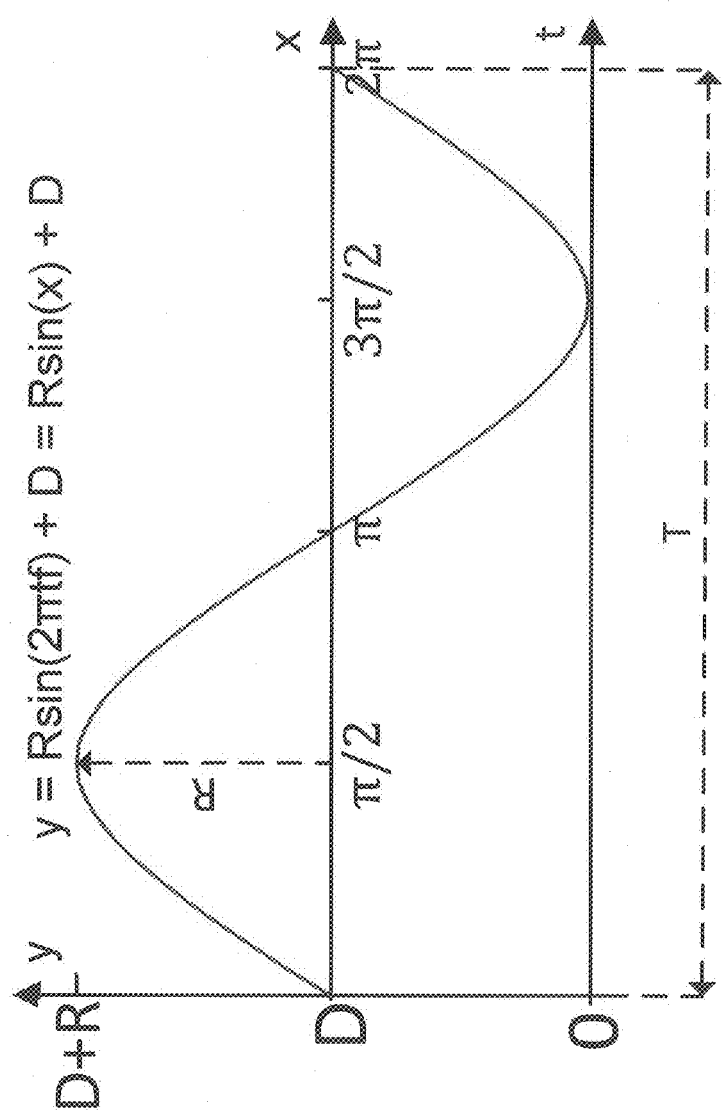
FIG. 5 is the filtered drive/excitation signal for the piston/bob driving coil.

Referring now to FIG. 2, the control circuitry 24 is shown. The heart of the control circuitry 24 is the controller 26. The controller 26 generates a digitally-synthesized sine wave by use of an internal, crystal-controlled oscillator. The signal generated by the controller 26 filtered by the low-pass filter 28 is shown in FIG. 5, which has high amplitude and frequency stability.

The signal being delivered by the controller 26 to the low-pass filter 28 has a DC component and a sinusoidal component.

The combined DC voltage with the filtered sine wave is fed to voltage-to-current converter 30.

The controller 26 operates a coil selector 32 to determine which of the coils 12 or 14 is going to be the driving/excitation coil with the other being the sensing coil. Assume that coil A (previously referred to as coil 12) is selected by the coil selector 32 to be the driving/excitation coil. In that case, coil A (12) will have a DC component and a sinusoidal component applied thereto. Coil B (previously referred to as coil 14) sensing a large induced sine wave that has little or no DC offset. As coil A (12) causes the ferromagnetic bob 22 (see FIG. 1) to move, the amount of the movement is sensed in coil B (14). The movement of the reciprocating bob 22 changes the mutual inductance between the coils 12 and 14.

A very accurate voltage reference 34 is provided so that when coil A (12) or coil B (14) is selected for the sensing function (the other coil having been selected for the driving/excitation function), then the corresponding comparator A or B is also selected.

Assuming that controller 26 has set the coil selector 32 to disconnect coil B (14) from the voltage-to-current converter 30 and connect coil A (12) thereto instead. As the sine wave modulated current from the voltage-to-current convertor 30 flows through coil A (12), the magnetic field pulls the ferromagnetic bob 22 (see FIG. 1) into the sample well 18, and a sine wave signal is induced into coil B (14). The sine wave induced in coil B (14) is shown in the right-hand side of FIG. 3. This sine wave is fed to comparator B (38) where it is compared against voltage reference 34. The voltage reference 34 is the same as the "comparator threshold Y" illustrated in FIG. 3. The output of comparator B (38) is converted to a peak amplitude for each period of the sine wave using the following equations and correspondences:

$$y = R \sin(2\pi t f) \quad (1)$$

$$T = 1/f \quad (2)$$

$$2\pi \equiv T \quad (3)$$

$$2(\pi/2 - \alpha) \equiv t_c \quad (4)$$

$$\alpha = \pi/2 - \pi T_c/t \quad (5)$$

$$\alpha = \pi/2 - \pi t_c f \quad (6)$$

$$\sin \alpha = \cos(\pi t_c f) \quad (7)$$

$$R = Y/\sin \alpha \quad (8)$$

$$R = Y/\cos(\pi t_c f) \quad (9)$$

Figure 4:
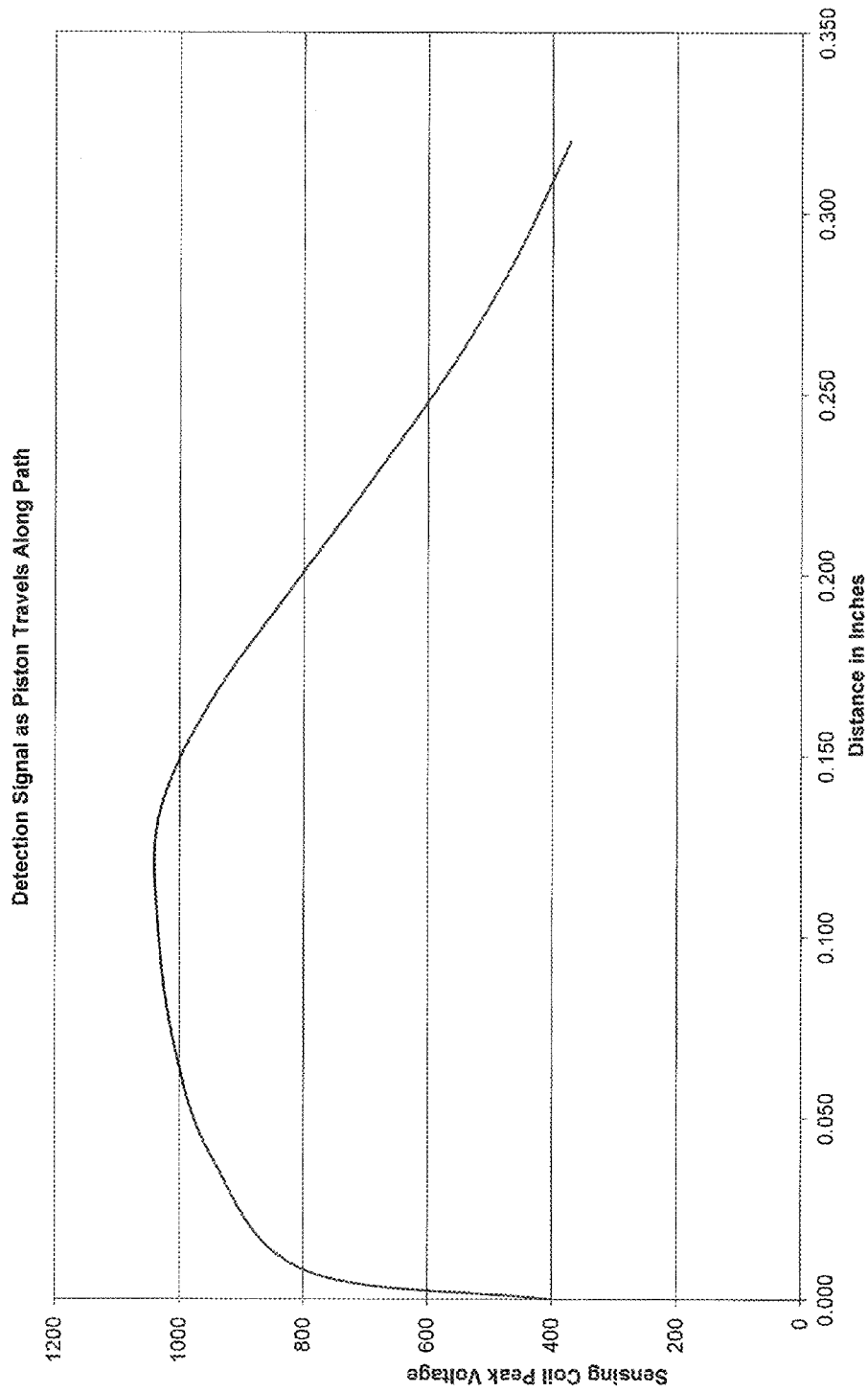
FIG. 4 is a plot of the viscometer's sensor-coil output as a function of bob travel.

The peak amplitudes are processed by the controller 26 to create the sine wave envelope as shown in FIG. 4. FIG. 4 determines the position of the ferromagnetic bob 22 as it travels inside of coil A (12).

Once the controller 26 determines the ferromagnetic bob 22 has traveled far enough in the direction of coil A (12), the controller 26 records the end travel time and swaps the coils' roles in the coil selector 32 so that now coil B (14) is the driving coil and coil A (12) is the sensing coil. The travel time is reset at this point. The ferromagnetic bob 22 will now travel in the opposite direction with comparator A (36) detecting the position of the ferromagnetic bob 22. This process may be repeated for as many cycles as required.

Connected to the controller 26 is a data/parameter RAM 40. Data/parameter RAM 40 provides a non-volatile RAM that can store internal parameters to be used by the firmware or measurement set up parameters. Also, the data/parameter RAM 40 may also be used to store data. While many different types of memory can be used in the present invention, a FRAM (Ferroelectric Random Access Memory) is the preferred memory device due to its extremely high endurance and very fast read and write speeds. The settings to generate the drive/excitation signals can also be stored in the data/parameter RAM 40.

The measurements made and recorded in the controller 26 may be shown on the display 42. An operator can get an instantaneous feedback as to whether the reciprocating bob sensor 10 is operating properly.

The controller 26 may be accessed through wireless connectivity interfaces 44 or through a wire connectivity/storage interfaces 46. Any changes to the test being run can be made through the process control interfaces 48.

Referring to FIGS. 1 and 4 in combination, the distance the ferromagnetic bob 22 travels has been plotted versus the voltage being applied. This shows where the ferromagnetic bob 22 is within the sample well 18. Once the ferromagnetic bob 22 has reached a certain point, the controller 26, through the coil selector 32, will reverse the functions of coil A (12) and coil B (14) and, respectively, comparator B (38) and comparator A (36). There is very little or no DC offset in the sensing coil, whether coil A (12) or coil B (14). The distance the ferromagnetic bob 22 travels can be very accurately determined due to the high accuracy sinusoidal-based excitation/detect mechanism. The plot shown in FIG. 4 provides the positional information for ferromagnetic bob 22 as it travels through coil A (12) and coil B (14).

Additionally, coil A (12) and coil B (14) have a resonance circuit therein which acts as a natural amplifier when operating near the resonance frequency.

Figure 3:
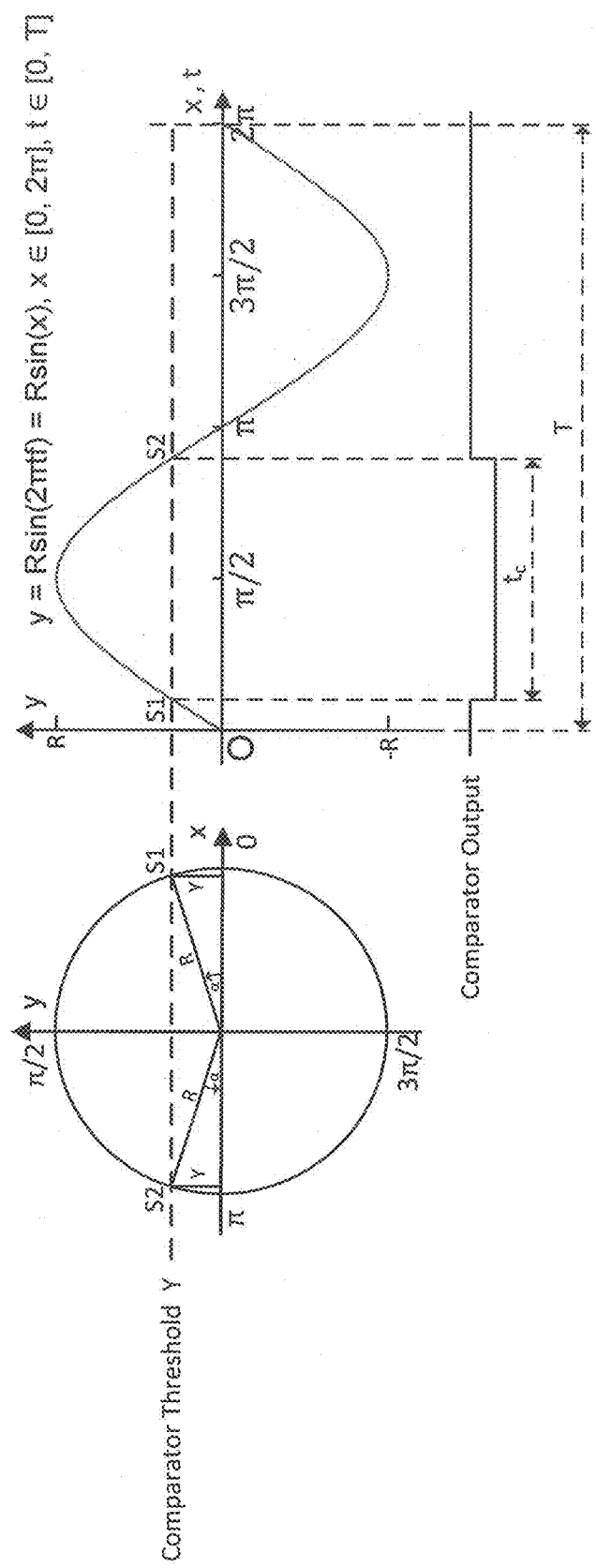
FIG. 3 is the signal induced in the piston/bob sensing coil.

Referring to FIG. 3 in combination with the equations given herein above, peak amplitude R for each period of the sine wave can be derived with the use of either comparator A (36) or comparator B (38). The sine wave function is defined by the following equation:

$$y = R\sin(2\pi t f) \quad (1)$$

$$T = 1/f \quad (2)$$

where R is the peak voltage, y is the instantaneous voltage signal amplitude, f is the frequency, T is the period (or the reciprocal of frequency) and t is the time. The time t varies between 0 and T. The comparator (comparator A or comparator B) compares the sine wave signal with a DC voltage level Y, also called the "comparator threshold." When the sine wave amplitude is higher than the comparator threshold, the comparator output (from either comparator A or comparator B) is low, as illustrated by the letter $t_c$ shown in the right-side timing diagram of FIG. 3.

The left-side diagram of FIG. 3 is the angular representation of the same sine wave, mapped in a circle of radius R, which rotates counterclockwise as the time t increases from 0 to T. Thus, the period of time $t_c$ corresponds to the concave angle between the radii R. The magnitude of this angle is defined by the following correspondence:

$$2(\pi/2 - \alpha) \equiv t_c \quad (4)$$

The proportion defined by the following correspondences $$2\pi \equiv T \quad (3)$$

$$2(\pi/2 - \alpha) \equiv T \quad (4)$$

is used to calculate the angle α, which is shown in the following equations:

$$\alpha = \pi/2 - \pi t_c/T \quad (5)$$

$$\alpha = \pi/2 - \pi t_c f \quad (6)$$

As can be seen from the left-side angular diagram in FIG. 3, the following equation $$\sin \alpha = Y/R$$

can be used to derive the sinusoid peak amplitude R as defined by the following equation $$R = Y/\sin \alpha \quad (8)$$

From trigonometry, one can calculate the angle shown as follows:

$$\sin \alpha = \cos(\pi t_c f) \quad (7)$$

Combining equations 7 and 8 yields the following:

$$R = Y/\sin \alpha = Y/\cos(\pi t_c f) \quad (9)$$

Since the sine wave frequency f is defined, the period of time $t_c$ during which the comparator output is low can be used to calculate the peak amplitude R of the sine wave.

By using the wave forms as just described in conjunction with FIG. 3, a sinusoidal component of relatively high amplitude as shown in FIG. 5 is used to energize the driving coil (coil A or coil B) which induces a much higher voltage signal in the sensing coil (the other of coil A or coil B). This and the proximity of the sine wave frequency to the sensing coil resonance frequency eliminate the need for amplification of the sensing coil signal. By eliminating the need for amplification, there is a significant reduction in noise along with inherent offsets or drifts that normally exist in analog circuits. By eliminating the need for amplification, the controller 26 can accurately measure position and velocity of the reciprocating bob 22 (see FIG. 4). The added precision allows the viscosity of a fluid/gas to be determined over a much shorter portion of the reciprocating bob's travel path, which could not be done with prior designs.

What I claim is:

1. A reciprocating bob viscometer having
   A. a mechanical structure including:
      i. a sample well
      ii. a ferromagnetic bob located in a sample well for reciprocating in first and second directions along a bob path in said sample well, and
      iii. first and second coils disposed with respect to the sample well so that current through the first coil results in the magnetic force that tends to drive the ferromagnetic bob in a first direction, that current driven through the second coil results in a magnetic force that tends to drive the bob in a second direction, mutual inductance between the first and second coils depends on the position of the ferromagnetic bob;
   B. the control circuitry including:
      i. a driving circuitry for sending a driving current through the first coil to drive the ferromagnetic bob in a first direction through fluid or gas contained in the sample well;
      ii. sensing circuitry for sensing an output signal from the second coil caused by said mutual inductance between the first and second coils;
      iii. controller for generating from said output signal a characterized output that represents the shear stress on the fluid/gas as a function of the sheering that the fluid/gas undergoes;
   the improvement comprising:
   said driving current is a digitally generated near resonance frequency sinusoidal signal where the sine wave is defined by:

$$y = R\sin(2\pi t f)$$

where "R" is the peak voltage, "y" is the instantaneous voltage signal amplitude, "t" is the time and "f" is the frequency with a DC voltage level of Y;
   said peak voltage R being determined by:

$$R = Y/\cos(\pi t_c f)$$

where $t_c$ being time output is above a comparator output level;
   wherein said peak amplitude for said period of said sinusoid signal is processed in said controller to determine the position of said ferromagnetic bob in said sample well;
   wherein roles of said first coil and said second coil are reversed using a coil selector when said ferromagnetic bob has travelled far enough in said first direction in said sample well; and
   wherein said first and second coils have a resonance circuit therein to act as a natural amplifier because operation thereof is near the resonance frequency.

* * * * *